United States Patent

Nikam

Patent Number: 6,063,774
Date of Patent: May 16, 2000

[54] TRICYCLIC QUINOXALINE DERIVATIVES AS NEUROPROTECTIVE AGENTS

[75] Inventor: Sham Nikam, Ann Arbor, Mich.

[73] Assignee: Warner-Lambert Company, Morris Plains, N.J.

[21] Appl. No.: 09/066,375

[22] PCT Filed: Dec. 15, 1997

[86] PCT No.: PCT/US97/23254

§ 371 Date: Apr. 29, 1998

§ 102(e) Date: Apr. 29, 1998

[87] PCT Pub. No.: WO98/27097

PCT Pub. Date: Jun. 25, 1998

Related U.S. Application Data

[60] Provisional application No. 60/032,979, Dec. 16, 1996.

[51] Int. Cl.[7] ............ A61K 31/495; C07D 487/14
[52] U.S. Cl. ............ 514/81; 514/220; 540/460; 540/497; 544/244; 544/250
[58] Field of Search .................... 540/460, 497, 540/471, 559; 544/244, 250; 514/250, 81, 220

[56] References Cited

U.S. PATENT DOCUMENTS

| | | | |
|---|---|---|---|
| 5,532,236 | 7/1996 | Jacobsen et al. | 514/228.5 |
| 5,574,038 | 11/1996 | Jacobsen | 514/249 |

FOREIGN PATENT DOCUMENTS

| | | |
|---|---|---|
| 0627434 | 12/1994 | European Pat. Off. . |
| 0705834 | 4/1996 | European Pat. Off. . |
| 0705835 | 4/1996 | European Pat. Off. . |
| 9308188 | 4/1993 | WIPO . |
| 9425472 | 11/1994 | WIPO . |
| 9426747 | 11/1994 | WIPO . |
| 9512417 | 5/1995 | WIPO . |

OTHER PUBLICATIONS

Kukla et al. Synthesis and Anti HiV activity . . . J. Med. Chem. 34, 3187–3197, 1991.

Lipton, S. Prospects for clinically tolerated NMDA antagonists . . . TINS. 16(12), 527–532, 1993.

Lees, G.J. Therapeutic Potential of AMPA Receptor Ligands . . . CNS Drugs 5(1) 51–74, 1996.

Doble, A. Excitatory aminoacid receptors and neurodegeneration. Therapie 50, 319–337, 1995.

PCT International Search Report PCT/US97/23254.

Moon et al., "Dopaminergic and Serotonergic Activities of Imidazoquinolinones and Related Compounds", *J. Med. Chem.*, 1992, 35, pp. 1076–1092.

Nagata et al., "Structure–Activity Relationships of Tricyclic Quinoxalinediones as Potent Antagonists for the Glycine Binding Site of the NMDA Receptor 1", *Bioorganic & Medicinal Chemisty Letters*, 1995, vol. 5, No. 14, pp. 1527–1532.

Nagata et al., "Structure–Activity Relationships of Tricyclic Quinoxalinediones as Potent Antagonists for the Glycine Binding Site of the NMDA Receptor 2", *Biorganic & Medicinal Chemistry Letters*, 1995, vol. 5, No. 14, pp. 1533–1536.

Nagata et al., "Tricyclic Quinoxalinediones: 5,6–Dihydro–1H–pyrrolo[1,2,3–de]quinoxaline–2,3–diones and 6,7–Dihydro–1H,5H–pyrido[1,2,3–de]quinoxaline–2,3–diones as Potent Antagonists for the Glycine Binding Site of the NMDA Receptor", *J. Med. Chem.*, 1994, 37, pp. 3956–3968.

Kornhuber et al. "Psychotogenicity and N–methyl–D–aspartate Receptor Antagonism: Implications for Neuroprotective Pharmacotherapy" Biol Psychiatry (1997) 41, 135–144, 1997.

Primary Examiner—Richard L. Raymond
Assistant Examiner—V Balasubramanian
Attorney, Agent, or Firm—Elizabeth M. Anderson

[57] ABSTRACT

Neuroprotective agents have forumula I

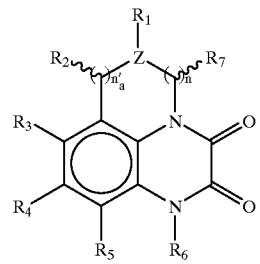

Formula I wherein a is a ring of 6 to 8 members;

n and n' are 1 or 2, $R_2$ is hydrogen or oxygen of carbonyl, $R_1$, $R_2$, $R_3$, $R_4$, $R_5$ and $R_6$ independently include hydrogen, alkyl, aralkyl, and carboxyalkyl.

8 Claims, 1 Drawing Sheet

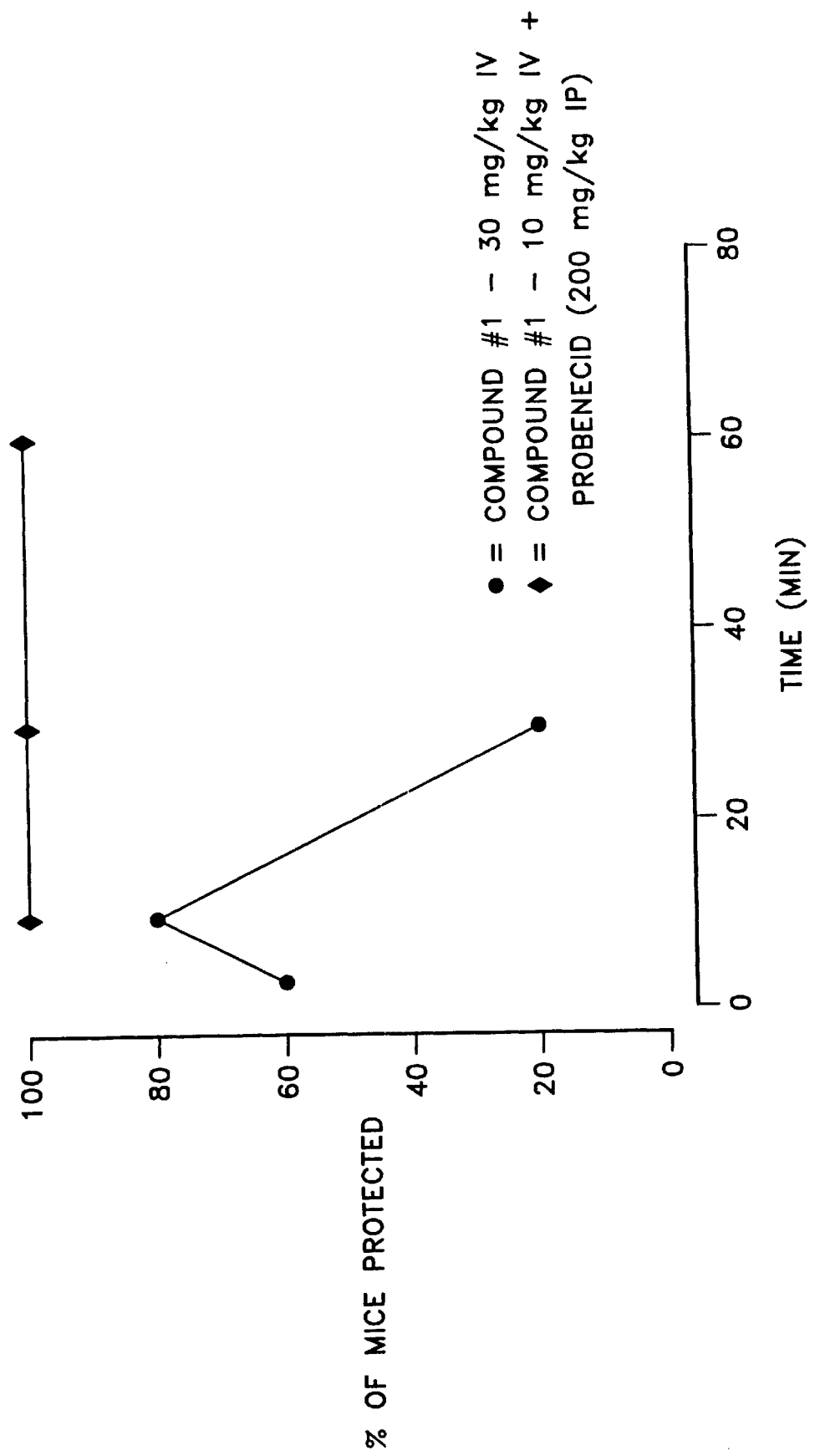

TRICYCLIC QUINOXALINE DERIVATIVES AS NEUROPROTECTIVE AGENTS

This application is a §371 application of PCT/US97/23254, filed Dec. 15, 1997 which claims the benefit of U.S. Provisional Application No. 60/032,979 filed Dec. 16, 1996.

FIELD OF THE INVENTION

The invention pertains to tricyclic quinoxaline derivatives that are neuroprotective agents. In particular, the invention pertains to AMPA (alpha-amino-3-hydroxy-5-methyl-4-isoxazole propionic acid) receptor and glutamate antagonists (NMDA antagonists, i.e., n-methyl-D-aspartate).

BACKGROUND OF THE INVENTION

Over excitation of NMDA receptor channel complexes on postsynaptic neurons following excessive release of glutamic acid from synaptosomes and glutamic acid from synaptosomes and glial cells results in a massive calcium ion influx into the neuronal cells, which leads to their death. This is believed to occur under ischemic or hypoxic conditions such as stroke, hypoglycemic, cardiac arrest and physical trauma. An NMDA receptor antagonist might be therapeutically useful because it may minimize damage of the central nervous system induced by ischemic or hypoxic conditions. The NMDA receptor channel complex consists of at least three binding domains including glutamic acid (or NMDA) recognition site, channel blocking binding site, and strychnine-insensitive glycine binding type. Physiologically, a blockade of at least one of these sites terminates the channel opening of the NMDA receptor to prevent a calcium ion influx *J. Med. Chem.*, 1994;37:3956–3968, R. Nagata, et al.

Excessive excitation by neurotransmitters may be responsible for the loss of neurons in cerebral vascular disorders such as cerebral ischemia or cerebral infarction resulting in a range of conditions such as thromboembolic or hemorrhagic stroke, cerebral vasospasm, hypoglycemia, cardiac arrest, status epilepticus, perinatal, asphyxia anoxia, such as from near drowning, pulmonary surgery, and cerebral trauma, as well as lathyrism, Alzheimer's disease, and Huntington's disease. Such conditions likewise suggest the use of agents that may act as antagonists in the receptors identified above may lead to treatment of Amyotrophic lateral sclerosis (ALS), schizophrenia, Parkinsonism, epilepsy, anxiety, pain, and drug addiction. PCT/EPO 94/01492 having publication number WO94/26747 published Nov. 24, 1994, Watjen, et al.

L-glutamic acid, L-aspartic acid, and a number of other closely related amino acids have the ability to activate neurons in the nervous system. Therefor the vast majority of excitatory neurons in the mammalian CNS. Interaction with glutamic acid mediated neurotransmission is considered a useful approach in the treatment of neurological and psychiatric diseases. WO94/26746, published Nov. 24, 1994, Jacobsen, et al.

Tricyclic quinoxaline diones as glutamate receptor antagonists are described in WO93/08188, published Apr. 29, 1993, R. Magata, et al.

WO92/22552, published Dec. 23, 1992, Tenbrink, et al., discloses imidazolo quinoxaline materials that are useful an anxiolytic and sedative/hypnotic agents.

European Patent Application 627,434, published Dec. 7, 1994, R. Nagata, et al., discloses tricyclic quinoxaline dione derivatives which are selective antagonists of the glycine binding site of the NMDA receptor.

It is an object of the present invention to disclose AMPA/GLY antagonists which are useful as neuroprotective agents.

It is a further object of the present invention to describe novel conformationally constrained tricyclic quinoxaline dione derivatives.

SUMMARY OF THE INVENTION

Described are tricyclic quinoxaline dione compositions of Formula I

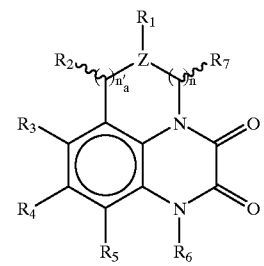

wherein a is a ring of 6 to 8 members;
n or n' independently is an integer of from 1 to 2;
Z is CH, oxygen, or nitrogen;
$R_1$ is hydrogen,
    alkyl of from 1 to 6 carbon atoms,
    aralkyl of from 7 to 12 carbon atoms,
    carboxyalkyl of from 2 to 8 carbon atoms,
    phosphoralkyl of from 1 to 6 carbon atoms, or
    phosphonalkyl of from 1 to 6 carbon atoms;
$R_2$ is H or oxygen of carbonyl;
$R_3$ is hydrogen,
    alkyl of from 1 to 6 carbon atoms,
    alkenyl of from 3 to 6 carbon atoms,
    cycloalkyl of from 5 to 7 carbon atoms,
    halogen,
    haloalkyl of from 1 to 6 carbon atoms,
    aryl of from 6 to 12 carbon atoms,
    aralkyl of from 7 to 12 carbon atoms,
    heteroaryl of from 5 to 8 members which may contain nitrogen, oxygen, or sulfur,
    heterocycloalkyl of from 4 to 7 members,
    nitro,
    cyano,
    $SO_2CF_3$,
    $(CH_2)_m CO_2R_8$,
    $(CH_2)_m CONR_8R_9$,
    $SONR_8R_9$, or
    $NHCOR_8$;
$R_4$ and $R_5$ are each independently
    hydrogen,
    alkyl of from 1 to 6 carbon atoms,
    cycloalkyl of from 5 to 7 carbon atoms,
    alkenyl of from 3 to 6 carbon atoms,
    halogen,
    haloalkyl of from 1 to 6 carbon atoms,
    nitro,
    cyano,
    $SO_2CF_3$,
    $CH_2SO_2R_{10}$,
    $(CH_2)_m CO_2R_{10}$,
    $(CH_2)_m CONR_{11}R_{12}$,
    $(CH_2)_m SO_2NR_{11}R_{12}$, or
    $NHCOR_6$;
wherein m is an integer of from 0 to 4, and $R_6$ is hydrogen, hydroxy, or amino;

$R_7$ is hydrogen,
  alkyl of from 1 to 6 carbon atoms,
  aralkyl of from 7 to 12 carbon atoms,
  cycloalkyl of from 5 to 7 carbon atoms,
  aryl of from 6 to 12 carbon atoms,
  heteroaryl of from 5 to 8 atoms containing oxygen, nitrogen, or sulfur,
  heterocycloalkyl of from 4 to 7 members, or
  oxygen of carbonyl group;

$R_8$ and $R_9$ are each independently hydrogen,
  alkyl of from 1 to 6 carbon atoms,
  cycloalkyl of from 5 to 7 carbon atoms,
  haloalkyl of from 1 to 6 carbon atoms,
  aralkyl of from 7 to 12 carbon atoms; and $R_{10}$, $R_{11}$, and $R_{12}$ are each independently selected from hydrogen,
  alkyl of from 1 to 6 carbon atoms,
  cycloalkyl of from 5 to 7 carbon atoms,
  haloalkyl of from 1 to 6 carbon atoms, or
  aralkyl of from 7 to 12 carbon atoms;

or a pharmaceutical salt thereof.

Also described are tricyclic quinoxaline dione compositions of Formula I with the further definition that when ring a is a 7- or 8-membered ring, $R_7$ may also be —$N(R_1)_2$, —$SONR_8R_9$, or —$NHCOR_8$.

Also described is a method for or treatment of neurodegenerative disorders including ALS, stroke such as thromboembolic or hemorrhagic, hypoglycemic conditions, cardiac arrest, trauma, ischemia, cerebral infarction, status epilepticus, perinatal, asphyxia anoxia, Lathyrism, Alzheimer's disease, Huntington's disease, schizophrenia, Parkinsonism, epilepsy, anxiety, pain, and drug addiction, comprising administering to a mammal in need thereof a therapeutically effective amount of a compound of Formula I.

BRIEF DESCRIPTION OF THE DRAWINGS

FIG. 1 plots maximal electroshock time course with Compound 1 of the invention, with and without probenecid pretreatment in mice.

DESCRIPTION OF PREFERRED EMBODIMENT

The present invention is concerned with compounds of Formula I.

Some of the compounds of Formula I are capable of further forming both pharmaceutically acceptable acid addition and/or base salts. These forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, flimarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, isethionate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention may exist as a mixture of cis and trans isomers or as the individual cis and trans isomers or R and S stereoisomers. The mixture of isomers as well as the individual isomers are intended to be encompassed within the scope of the present invention.

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "carboxyalkyl" means alkyl as above and attached to a carboxy group.

The term "phosphoroalkyl" means alkyl as above and attached to a phosphoro group.

The term "phosphonoalkyl" means alkyl as above and attached to a phosphoro group.

The term "alkenyl" means a straight or branched unsaturated hydrocarbon radical having from 3 to 6 carbon atoms and includes, for example, 2-propenyl, 1-butenyl, 2-butenyl, 1-pentenyl, 2-pentenyl, 3-methyl-3-butenyl, 1-hexenyl, 2-hexenyl, 3-hexenyl and the like.

"Alkoxy" or "thioalkoxy" is O-alkyl or S-alkyl of from 1 to 6 carbon atoms as defined above for "alkyl".

The term "aryl" means an aromatic radical which is a phenyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, or 1,3-benzodioxol-5-yl.

The term "aralkyl" means aryl and alkyl as defined above and includes but is not limited to benzyl, 2-phenylethyl, and 3-phenylpropyl; a preferred group is phenyl.

The term "heteroaryl" means a heteroaromatic radical which is 2-, 3- or 4-pyridinyl, 2-, 4- or 5-pyrimidinyl, 2- or 3-thienyl, isoquinolines, quinolines, imidazolines, pyrroles, indoles, and thiazoles.

"Halogen" is fluorine, chlorine, bromine, or iodine.

The term "haloalkyl" means halogen and alkyl as defined above, for example, but not limited to, trifluoromethyl and trichloromethyl.

"Alkylaryl" means aryl as defined above and alkyl as defined above, for example, but not limited to benzyl, 2-phenylethyl, 3-phenylpropyl; a preferred group is benzyl.

The term "heterocycloalkyl" means a nonaromatic ring with from 4 to 7 members, with up to 4 heteroatoms for example, N, O, and S.

Common amino acid moiety means the naturally occurring α-amino acids, unnatural amino acids, substituted β, γ, Z amino acids and their enantiomers.

Common amino acids are: alanine, β-alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

Modified and unusual amino acids are as would occur to a skilled chemist and are, for example, but not limited to:
10,11-Dihydro-5H-dibenzo[a,d]cyclohepten-5-yl)glycine or α-amino-10,11-dihydro-5H-dibenzo[a,d]cycloheptene-5-acetic acid (Para-phenyl)phenylalanine,
3,3-Diphenylalanine,
3-Hydroxyproline,
4-Hydroxyproline,
N-Methylphenylalanine,
N-Methylaspartic acid,
N-Methylisoleucine,
N-Methylvaline,
Norvaline,
Norleucine,
Ornithine,
2-Aminobutyric acid,
2-Amino-4-pentanoic acid (Allylglycine),
$N^G$-Nitroarginine,
2-Amino-3-(2-amino-5-thiazole)propanoic acid,
2-Amino-3-cyclopropanepropanoic acid (Cyclopropylalanine),
Cyclohexylalanine (Hexahydrophenylalanine),
N-Methylcyclohexylalanine (N-Methylhexahydrophenylalanine),
2-Amino-4,4(RS)-epoxy-4-penntanoic acid,
$N^{im}$-2,4-Dinitrophenylhistidine,
2-Aminoadipic acid,
2-Amino-5-phenylpentanoic acid (Homophenyl-alanine),
Methionine sulfoxide,
Methionine sulfone,
3-(1'-Naphthyl)alanine,
3-(2'-Naphthyl)alanine,
2-Amino-3-cyanopropanoic acid (Cyuanoalanine),
Phenylglycine,
2-Aminopentanoic acid (Propylglycine),
2-Amino-6-(1-pyrrollo)-hexanoic acid,
2-Amino-3-(3-pyridyl)-propanoic acid (3-Pyridylalanine),
1,2,3,4-Tetrahydro-3-isoquinolinecarboxylic acid,
2-Amino-3-(4-thiazolyl)-propanoic acid,
O-Tertiary butyl-tyrosine,
O-Methyl-tyrosine,
O-Ethyl-tyrosine,
$N^{in}$-Formyl-tryptophan,
5H-Dibenzo[a,d]cycloheptene glycine,
9H-Thioxanthene glycine, and
9H-Xanthene glycine.

The compounds are prepared according to any one of the following schemes.

GENERAL EXPERIMENTAL

Scheme I

Step (a) of Scheme I above involves reacting arinobenzyl alcohol derivative of Formula I with a reactive acylating agent preferably phosgene in the presence of a tertiary base like triethylamine, inorganic or bater like sodium carbonate, sodium bicarbonate or potassium carbonate in a ethereal solvent preferably THF, or polar solvents like DMF, DMSO or water, preferably water at temperatures ranging from –10° C. to room temperature. The reaction mixture is stirred for 2 to 16 hours and diluted with water. Product is extracted with water insoluble solvent like ethyl acetate. The extracts washed with water and brine and dried over $MgSO_4$. The product was crystallized from solvent mixture preferably EtOAc and petroleum ether.

Step (b) involves bromination of the cyclic carbamate derivative of Formula II with a bromninating agent like bromine in a acidic solvent mixture like AcOH and TFA. The reaction is done at temperatures between 10° C. to room temperatures. Reaction mixture is stirred for around 2 hours and poured over ice-water. The precipitate is filtered and dried at elevated temperatures preferably at 120° C.

Step (c) involves the nitration of the bromo cyclic carbamate derivative as shown in Formula III with a nitrating agent like nitric acid or potassium nitrate preferably potassium nitrate in a acidic solvent like sulfuric acid at temperatures between 0° C. to room temperature. Reaction carried out for 4 to 16 hours preferably around 14 hours and poured over ice. The product precipitate was filtered and air dried.

Step (d) involves the reaction of the nitro cyclic carbamate derivative as shown in Formula IV with a secondary amine preferably N-methyl benzylamine. Reaction is carried out at elevated temperatures between 100° C. to 180° C. with or without a solvent like N-methyl formamide preferably without a solvent for about 18 hours. Volatile materials were evaporated under reduced pressure and the product isolated from the crude via column chromatography using pet.ether:EtOAc as the solvent mixture to give the desired benzylamine derivative.

Step (e) involves hydrogenation ($H_2$, around 50 psi) of the benzylamine derivative as shown in Formula V in the presence of a catalyst like Ra Ni and a base preferably KOH in a hydroxylated solvent like methanol. The catalyst is filtered off and the filtrate is evaporated to give the o-phenylene derivative, which is used in the next step without additional purification.

Step (f) involves reacting the o-phenylene diamine derivative as shown in Formula VI with a oxalic acid derivative like dimethyl oxalate in a hydroxylated or ethereal solvent preferably THF at reflux temperature. Reaction carried out for about 12 to 24 hours preferably 16 hours and partially evaporated to give a crude product which is purified by crystallization.

Step (g) involves hydrogenation ($H_2$, 50 psi) of the benzylamine quinoxaline 2,3-dione intermediate as shown in Formula VII using Pd/C (5–20%) preferably Pd/C (20%) as a catalyst in a polar solvent like DMF or methanol. The suspension was filtered, and the filtrate was evaporated to give a solid, which was crystallized form an hydroxylated solvent like methanol.

Step (h) involves nitration of the quinoxaline 2,3-dione derivative shown in Formula VIII using potassium nitrate or nitric acid preferably potassium nitrate as the nitrating agent. The reaction is carried out in a acidic solvent like sulfuric acid from temperatures ranging from 0° C. to room temperature. Reaction mixture is poured in ice, and the precipitate obtained is filtered and air dried.

Step (i) involves acylation followed by ring closure of quinoxaline 2,3-dione derivative shown in formula 9 using α-bromo acetyl bromide or chloride derivative in the presence of a base such as triethylamine. The reaction is carried out in a polar solvent like dimethylformamide at temperatures ranging from 0° C. to 50° C. preferably at room temperature under stirring. The reaction mixture was poured in water under stirring and the precipitate was filtered and air dried. Product was generally purified by column chromatography (SiO$_2$) using mixture of CHCL$_3$ and MeOH as eluent.

Step (j) involves cyclization reaction as outlined in step (i) of this scheme to synthesize substituted analogs of compound shown in formula 10. The reaction is carried out as outlined in step (i) of this scheme with the α,α'-disubstituted acylating agent with α substituent a halogen and α' substituent an alkyl, aryl, or aralkyl substituent. Product is isolated by aqueous workup and purified by crystallization or column chromatography (SiO$_2$), using a mixture of CHCl$_3$ and MeOH as eluant.

Scheme II

Step (a) involves acylation and cyclization of compound shown in formula I under conditions outlined in Scheme I step (i) with α,α-disubstituted haloacylhalide preferably dichloroacetylchloride as shown in formula 2. The compound as shown in formula 3 can be isolated by aqueous workup.

Step (b) involves amination of the α-halo compound as shown in formula 3 with primary or secondary amines optionally in the presence of organic bases such as triethylamine or inorganic bases such as potassium carbonate or potassium hydroxide in halogenated solvents such as dichloromethane or chloroform or ethereal solvents such as THF or polar solvents such as DMF. The product as shown in formula 4 can be isolated by a typical aqueous workup.

Scheme III

Step (a) involves nucleophilic ring opening of benzo[d][1,3]oxazin-2-one derivative as shown in formula 1 with amines preferably alkylamines such as methylamine under elevated temperatures or pressure, preferably pressure with low boiling amines such as N-methylamine.

Step (b) involves reacting benzylamine shown in formula 2 with acylating agent such as haloacylhalide preferably bromoacetyl bromide in the presence of organic bases such as triethylamine or inorganic bases like sodium carbonate, sodium bicarbonate or potassium carbonate in a ethereal solvent such as THF or polar solvent such as DMF. The product shown in formula 3 can be isolated by aqueous workup.

Step (c) involves intramolecular cyclization of the α-haloamide shown in formula 3 via the anion generation. The deprotonation of the amine can be carried out using a base such as sodium hydride, sodium methoxide, potassium tertiary butoxide, potassium hexamethylsilazide or lithium bases like LDA or LHMDS in solvents such as THF, ether or dioxane. The anion solution can be cyclized at temperatures ranging from room temperature to reflux preferably reflux temperatures. The cyclized product as shown in formula 4 can be isolated by aqueous workup.

Step (d) involves reduction of the nitro group in compound shown in formula 4 to the corresponding amine as shown in Compound 5. The reduction can be carried out as outlined in Scheme I, step (e).

Step (e) involves cyclization of the diamine derivative as shown in formula 5 to the corresponding quinoxaline 2,3-dione derivative as shown in formula 6 using an α-dicarbonyl reagent like oxalic acid derivatives under conditions outlined in Scheme I, step (f).

Step (f) involves nitration of the tricyclic derivative as shown in formula 6 to the corresponding nitrated compound as shown in formula 7. The nitration and isolation of the compound can be carried out as per the conditions outlined in Scheme I, step (h).

Scheme IV

Step (a) involves the nitration of appropriate o-dihalotoluene derivative shown in formula 1, preferably 2,6-dichloro-toluene using nitrating mixture like HNO$_3$/AcOH or KNO$_3$/H$_2$SO$_4$ preferably HNO$_3$/AcOH under stirring and temperatures ranging from 5° C. to room temperature. The reaction mixture is stirred for about 4 to 24 hours under completion and poured in ice water. The precipitate filtered and dried. Product can be crystallized from solvent like ethyl acetate or chloroform.

Step (b) involves the side-chain bromination of the methyl group of 2,6-dihalo-3-nitro-toluene intermediate shown in formula 2 using brominating agents like NBS in the presence of radical initiators like AIBN or dibenzoyl peroxide in solvents like carbon tetrachloride. Reaction can be carried out under stirring at temperatures from room temperature to reflux, preferably reflux for about 16 hours. On completion the reaction mixture can be cooled to room temperature and filtered. The filtrate on evaporation would give the crude bromomethyl derivative which can be purified by chromatography (SiO2, Pet.ether:EtOAc mixtures) to give the pure product.

Step (c) involves amination of the bromomethyl derivative from step (b) with N1-protected 1,2-diaminopropane derivative (R or R' are independently hydrogen, alkyl or carboxylic acid derivative), which can be optically pure or a racemate of formula 4 (PG=CBZ, Boc, Fmoc, C(O)CH$_3$) in the presence of a inorganic bases like sodium or potassium carbonate or sodium or potassium bicarbonate or organic bases like triethylamine and an inert solvent like halogenated hydrocarbon, e.g., chloroform or dichloromethane, an ethereal solvent like THF or dioxane at temperatures ranging from 0° C. to reflux temperatures. The desired product can be isolated by a typical aqueous workup and purified by crystallization or chromatography.

Step (d) involves the deprotection of the compound shown in formula 5. The product as shown in formula 5 on isolation can be deprotected using appropriate conditions, e.g., when PG=Boc, acids like HCl or H$_2$SO$_4$ can be used with or without a halogenated or ethereal solvent like chloroform or dioxane. The diamine as shown in product 6 can be isolated as an acid salt or as a free base.

Step (e) involves cyclization of the diamine shown in formula 6 in the presence of an inorganic or organic base like potassium or sodium carbonate, or trialkylamine such as triethylamine in chlorinated or non chlorinated solvents like chloroform, THF, methanol, or toluene. The reaction can be carried out at temperatures ranging from room temperature to reflux preferably at the reflux.

Step (f) involves reduction of the nitro group to the corresponding amino functionality in the compound as shown in formula 7. The reduction can be carried out under catalytic hydrogenation conditions using Pd/C or Ra—Ni as catalysts suspended in solvents like protic or ethereal solvents like methanol or THF at hydrogen pressures of about 50 psi, or in the presence of metal/acid mixture such as Fe/HCl or Sn/HCl. The o-phenylene diamine derivative can be isolated by using normal workup conditions and can be used in the next step without additional purification.

Step (g) involves cyclization of the o-phenylene diamine derivative as shown in formula 8 to form the quinoxalin 2,3-dione derivative as shown in formula 10. The cyclization can be carried out using oxalic acid or its activated esters or acid chloride in protic or ethereal solvents like aqueous HCl, methanol or THF under stirring at temperatures ranging from room temperature to reflux preferably temperatures of the reaction mixture.

Step (h) involves nitration of the compound shown in formula 10. Nitration can be carried out using nitrating mixtures like $HNO_3/AcOH$, $KNO_3/H_2SO_4$ or $NO_2BF_4/CH_2Cl_2$ preferably $KNO_3/H_2SO_4$. The product as shown in formula 11 can be isolated via normal aqueous workup and purified by crystallization or chromatography.

Scheme V

Step (a) involves reacting a activated benzyl alcohol (X=OH) as shown in formula 1 with appropriate α-amino acid derivative as shown in formula 2 under dehydrating conditions like Mitsunobu reaction using triaryl phosphine/dialkyl azodicarboxylate or reacting the amino derivative with the compound of formula 1 with X being a reactive leaving group such as chloro, bromo or sulfonyloxy derivative, e.g., methanesulfonyloxy, trifluorosulfonyloxy, 4-methylbenzenesulfonyloxy in an inert solvent like benzene, toluene, or THF. The reaction can be carried out at temperatures ranging from 5° C. to reflux preferably at room temperature for Mitsunobu reaction and higher temperatures for other leaving groups. The product can be isolated by crystallization or chromatography.

Step (b) involves reduction of the nitro group in compound shown in formula 2 and subsequently cyclize the diamino compound to form the compound shown in formula 4 under thermal conditions. The catalytic reduction can be carried out as a suspension of catalysts such as Ra Ni or Pd/C in protic or ethereal solvents like methanol or THF. In lieu of catalytic reduction metal/mineral acid system such as Fe/HCl and Zn/HCl can be used. The o-phenylene diamine intermediate can be heated in a protic or ethereal solvent like ethanol or THF at temperatures higher than 50° C., preferably at the reflux temperature of the reaction mixture.

Alternatively, the cyclization step can be carried out via anion generation as shown in step (c). The compound shown in formula 3 is treated with a base like NaH, or a alkali metal alkoxide such as KO-t-Bu or NaOMe in protic or ethereal solvents like ethanol, THF, or dioxane. The cyclization can then be effected by heating the reaction mixture over 50° C. preferably at the reflux. The nitro functionality in the cyclized product can then be reduced using the conditions in step (b).

Step (d) involves reduction of the amide carbonyl to the methylene linkage using hydride reagents such as LAH, $BH_3 \cdot THF$, or $AlH_3$. The reduction can be carried out in ethereal solvents like THF or ether at temperatures ranging from 0° C. to room temperature. Regular aqueous workup would give the desired benzodiazepinyl derivative as shown in formula 5.

Step (e) involves cyclization of the diamine derivative shown in formula 5 to the corresponding dione derivative as shown in formula 6. The cyclization can be carried out as discussed in Scheme I step (g).

Step (f) involves nitration of the dione derivative shown in formula 6 to give the nitrated compound as shown in formula 7. The nitration conditions have been outlined in Scheme I step (h).

Scheme VI

Step (a) involves reacting an activated benzyl alcohol (X=OH) as shown in formula 1 with appropriate N-methylamnino acetal derivative as shown in formula 2 under dehydrating conditions like Mitsunobu reaction using triaryl phosphine/dialkyl azodicarboxylate or reacting the amino derivative with the compound of formula 1 with X being a reactive leaving group such as chloro, bromo or a sulfonyloxy derivative, eg, methanesulfonyloxy, trifluorosulfonyloxy, 4-methylbenzenesulfonyloxy in an inert solvent like benzene, toluene, or THF. The reaction can be carried out at temperatures ranging from 5° C. to reflux preferably at room temperature for Mitsunobu reaction and higher temperatures for other leaving groups. The product as shown in formula 3 can be isolated by crystallization or chromatography.

Step (b) involves deprotecting the acetal under acidic conditions preferably using p-toluene sulfonic acid in a polar solvent like acetone at temperatures ranging from room temperature to reflux. The product as shown in formula 4 can be isolated as a free base by treatment with aqueous $NaHCO_3$ or triethylamine.

Steps (c) and (d) involve reduction of the nitro group in compound shown in formula 4 with simultaneous cyclization of the aldehyde functionality to give intermediate imine derivative as shown in formula 5. The reduction can be carried out as outlined in Scheme I step (e) and the imine intermediate can be futher reduced without isolation via catalytic reduction under similar catalytic hydrogenation conditions or using hydride reducing agents such as sodium borohydride or sodium cyanoborohydride to give the compound shown in formula 6.

Steps (e) and (f) involve cyclization of the diamine compound as shown in formula 6 to the dione derivative as shown in formula 7 and nitration of the dione derivative to the corresponding nitrated compound as shown in formula 8, respectively. The cyclization and nitration conditions are discussed in Scheme I steps (f) and (h) respectively.

Scheme VII

Step (a) involves alkylating benzyl alcohol derivative as shown in formula 1 with an α-halo acid derivative preferably methyl bromoacetate in the presence of alkali carbonate bases such as sodium carbonate, sodium bicarbonate, or potassium carbonate or organic bases such as triethyamine or pyridine in halogenated or nonhalogenated solvents such as chloroform, THF, acetone, or dioxane preferably acetone. The reaction can be carried out at temperatures between room temperature to reflux preferably at the reflux temperatures of the reaction mixture. The desired ether product as shown in formula 2 can be isolated on normal aqueous workup.

Step (b) involves reduction of the nitro group in the compound shown in formula 2 to the corresponding amine derivative followed by intramolecular cyclization to form the bicyclic compound as shown in Structure 3. The reductive cyclization conditions are similar to step (b) or (c) in Scheme V.

Step (c) involves reduction of the amide functionality in the compound shown in formula 3 using hydride reagents such as LAH or $BH_3 \cdot THF$, preferably LAH in a nonprotic ethereal solvent like THF or dioxane preferably at room temperature. The product as shown in formula 4 can be isolated by normal aqueous workup.

Alternatively step (d) depicts the synthesis of the bicyclic compound shown in formula 4 via anionic cyclization followed by reduction of the nitro group. The conditions for this cyclization have been elaborated in Scheme III step (c). The nitro group reduction as shown in step (e) to the corresponding amino derivative can be carried out under catalytic hydrogenation or metal/acid reducing systems as elaborated in Scheme I step (c).

Step (f) involves reduction of the amide functionality in the compound shown in formula 5 as per the conditions described in step (b) of this scheme to give the corresponding bicyclic derivative shown in formula 6.

Step (g) involves reduction of the nitro group in the compound shown in formula 6 to the corresponding amine shown in formula 4 using conditions outlined in Scheme I, step (e). Step (h) involves cyclization of the diamine derivative shown in formula 4 to the corresponding quinoxaline 2,3-dione derivative as shown in formula 7. This involves reacting the diamine derivative with oxalic acid or its activated derivatives like esters or acid chloride preferably dimethyl oxalate in a protic or ethereal solvent like methanol, ether, or THF, preferably THF at temperatures ranging from room temperature to reflux, preferably reflux temperatures of the reaction mixture. The product can be isolated by crystallization from the reaction solvent.

Step (i) involves nitration of the quinoxaline 2,3-dione derivative as depicted in formula 8. The nitration can be carried out as outlined in Scheme I step (h) to give the nitro product as shown in formula 8.

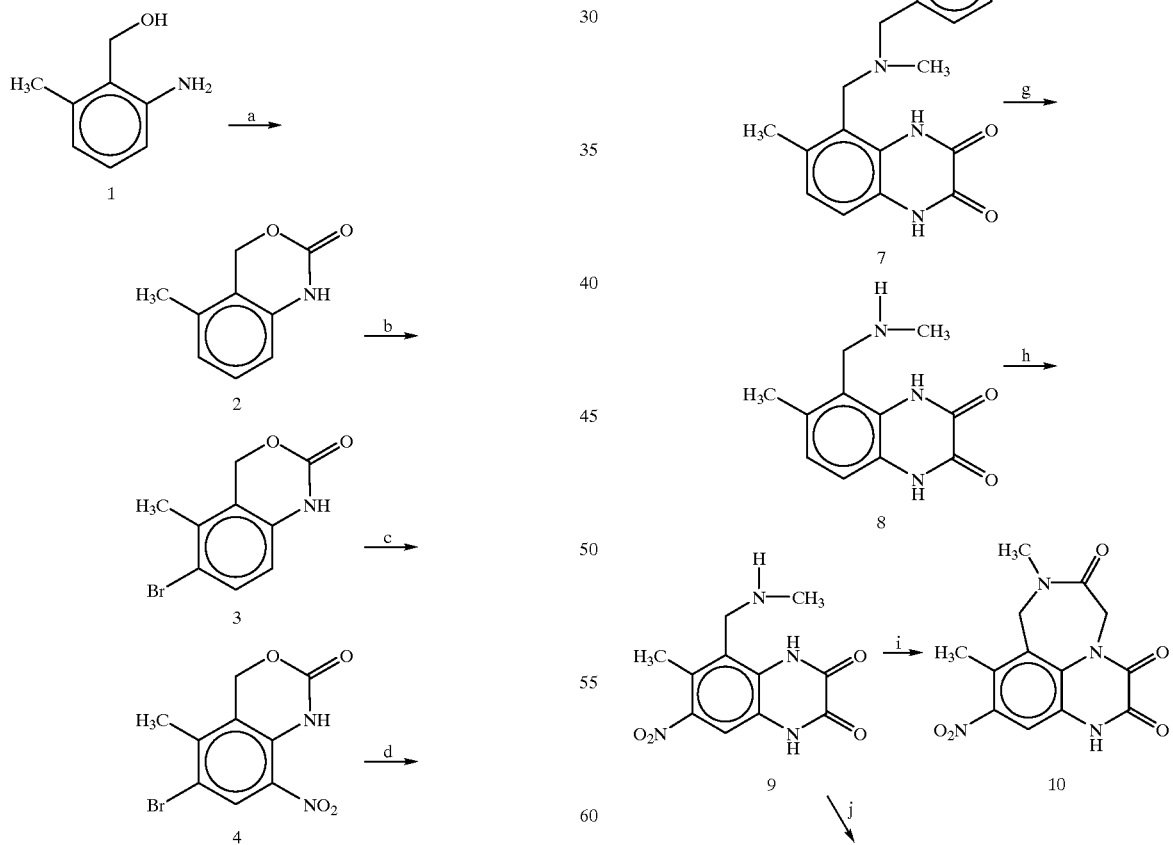

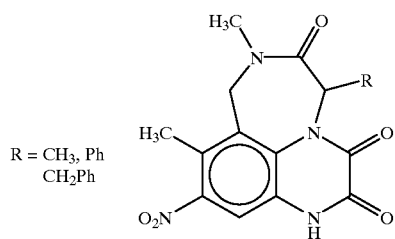
SCHEME II
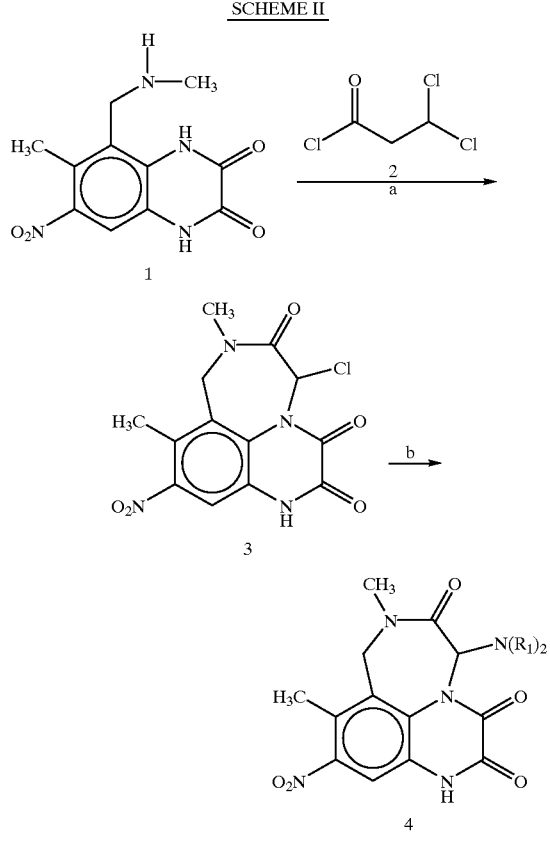
SCHEME III
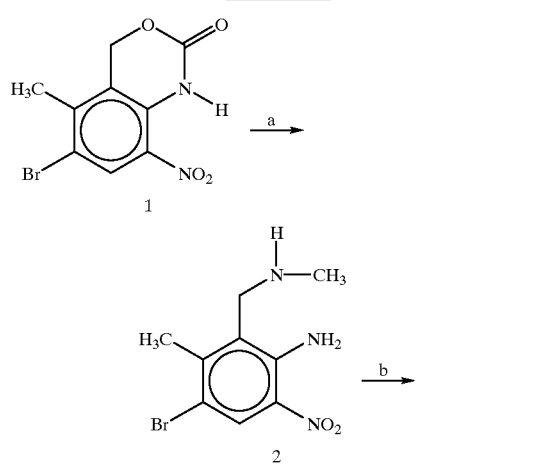
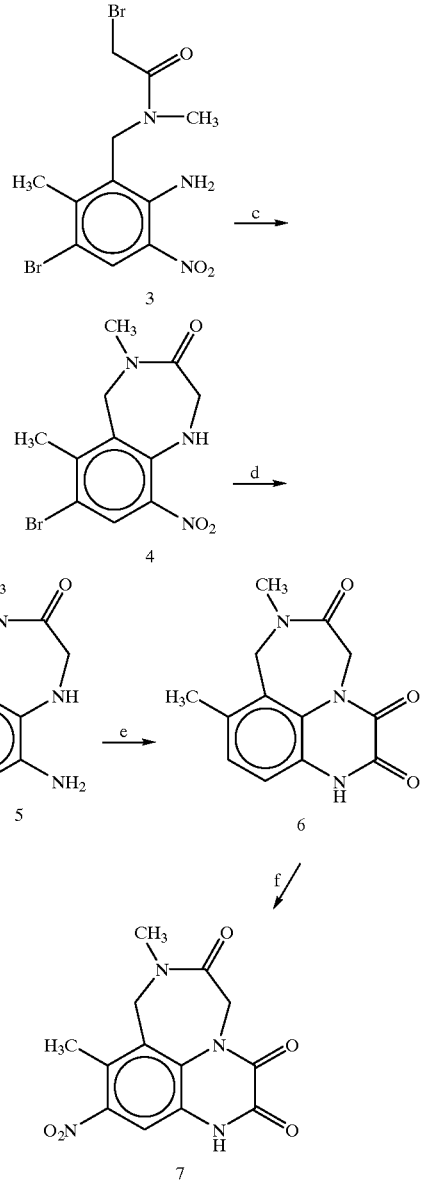
SCHEME IV
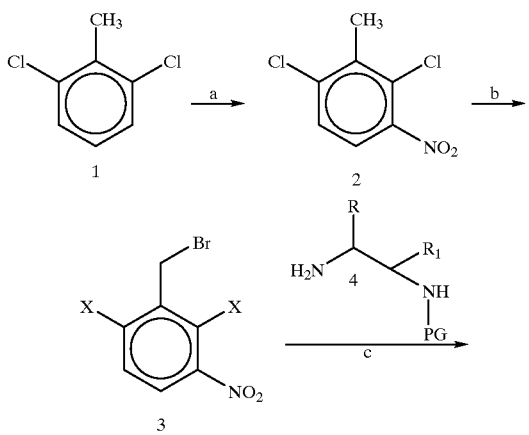

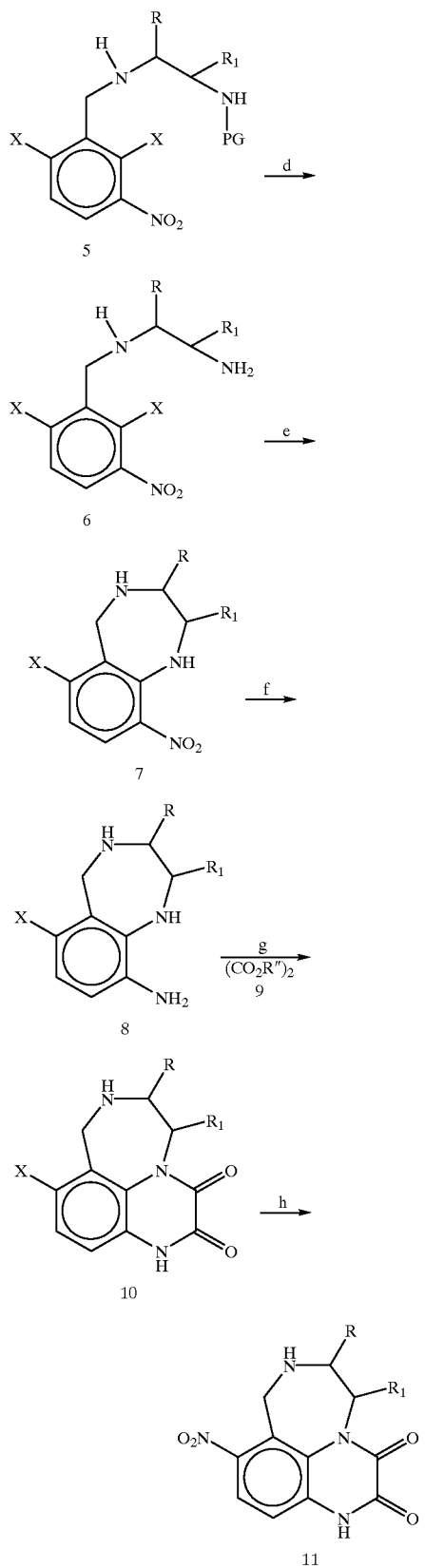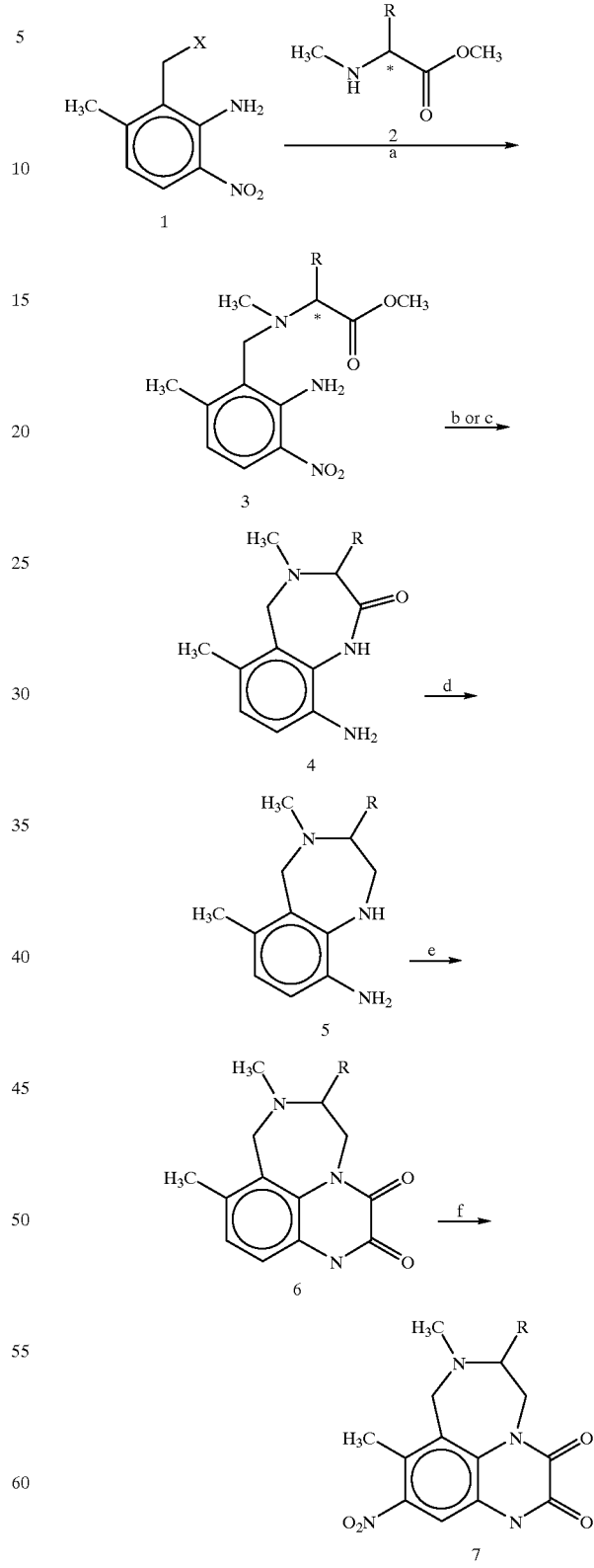
SCHEME V

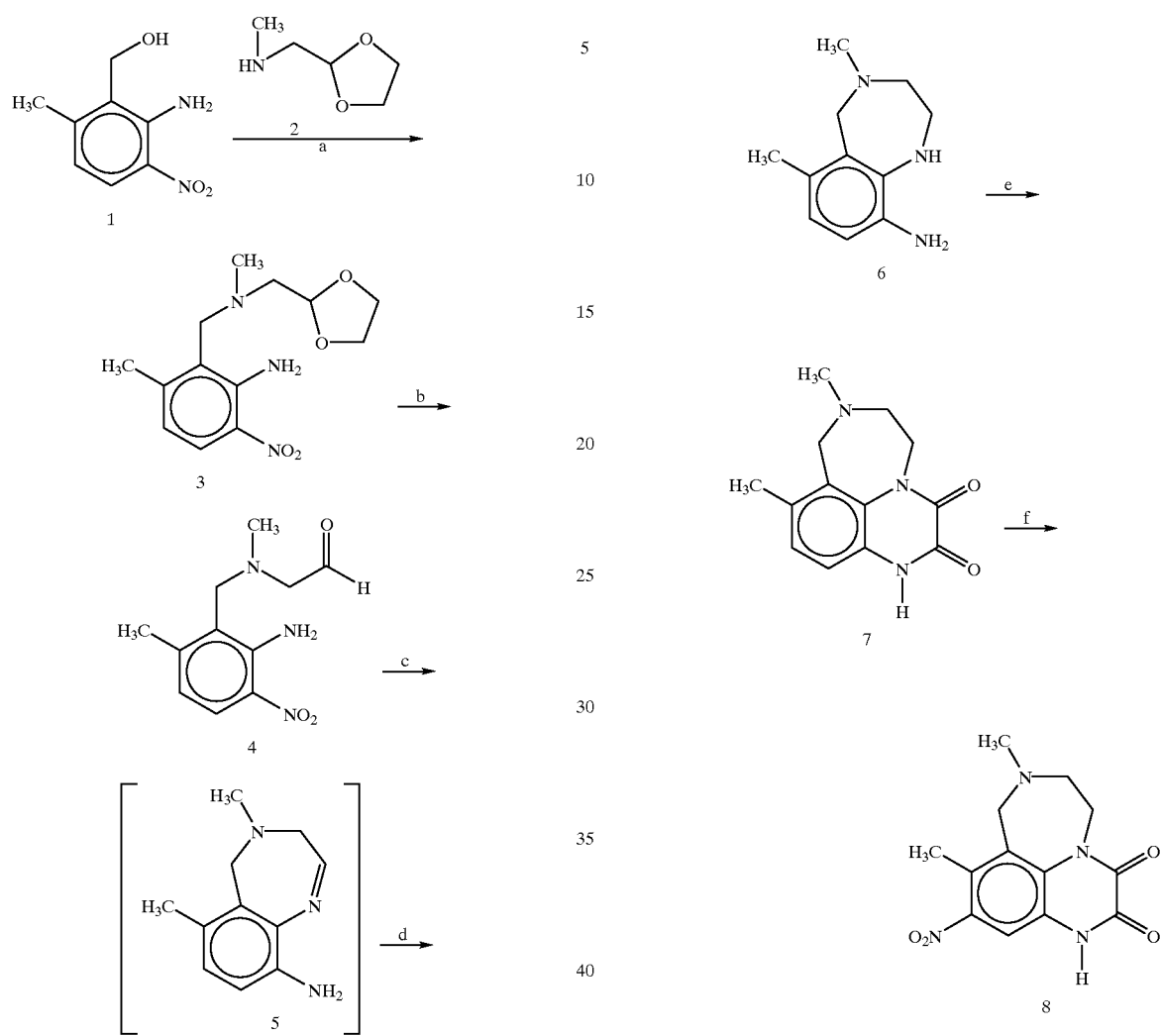
SCHEME VI
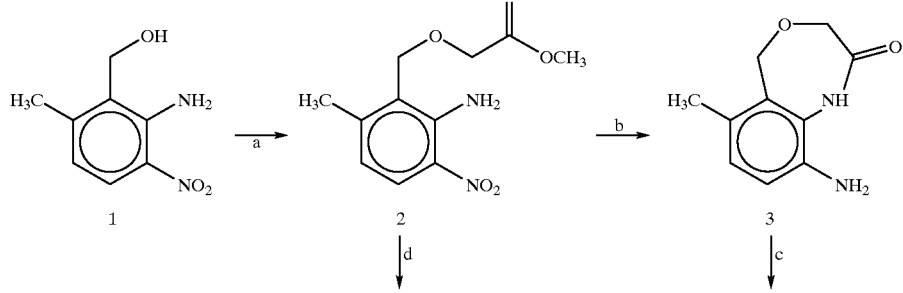
SCHEME VII

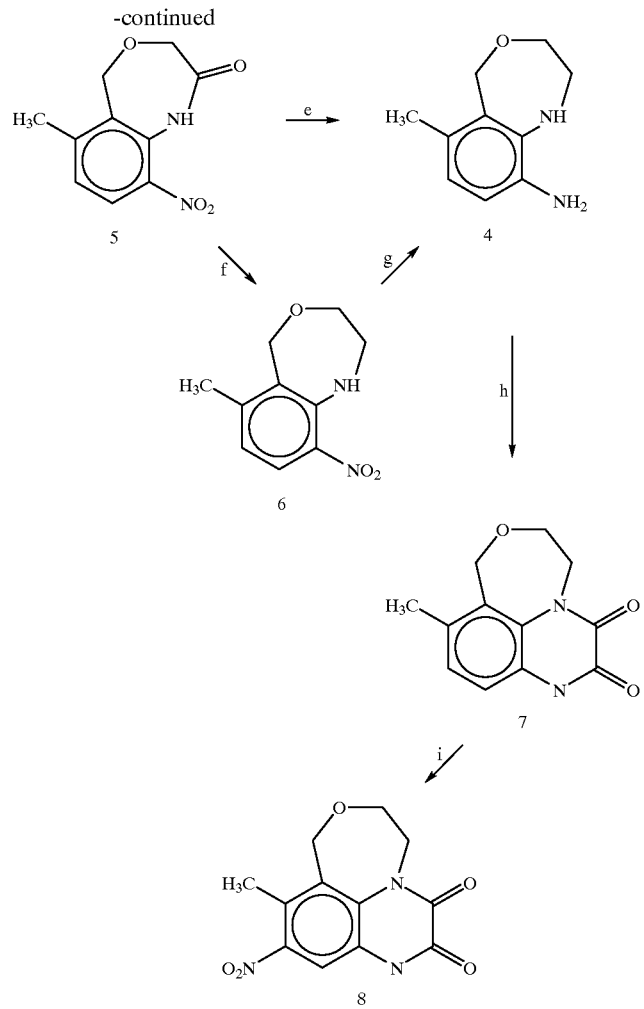

Preferred compounds of the invention are those of formula 1 above wherein:

a is a ring of 7 members;

n and n' are 1 and 2, respectively;

Z is nitrogen or oxygen;

$R_7$ is hydrogen,
 alkyl,
 aralkyl,
 cycloalkyl,
 aryl,
 oxygen of carbonyl, or
 heteroaryl;

$R_1$ is hydrogen or alkyl; and $R_2$ is hydrogen or the oxygen of a carbonyl group.

Some preferred structures are shown below.

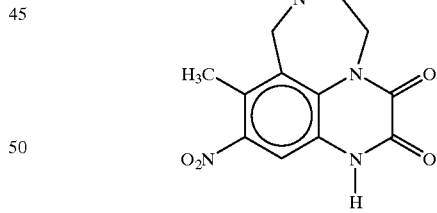

II

Other preferred structures are as follows:
1. Structures of Formula II except $R_7$ (—$CH_3$ attached to ring nitrogen) is —$CH_2C(O)OR$;
2. Structures of Formula II except $R_7$ (—$CH_3$ attached to ring nitrogen) is hydrogen;
3 to 5. Structures of Formula I having the following substituents:

| a | Z | $R_1$ | $R_2$ | $R_3$ | $R_4$ | $R_5$ | $R_6$ | $R_7$ |
|---|---|---|---|---|---|---|---|---|
| 7 | N | —$CH_3$ | H | —$CH_3$ | —$NO_2$ | H | H | H |
| 7 | O | — | H | —$CH_3$ | —$NO_2$ | H | H | =O |

The compounds of the present invention can be prepared and administered in a wide variety of routes of administration such as parenteral, oral, topical, rectal, inhalation, and the like. Formulations will vary according to the route of administration selected. Examples are oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. The following dosage forms may comprise as the active component, a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets; pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier can be a finely divided solid which is in a mixture with the finely divided active component.

In tablets, the active component can be mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component can be dispersed homogeneously therein, as by stirring. The molten homogenous mixture can be then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted for example from about 0.1 to 200 mg, preferably about 0.5 to 100 mg according to the particular application and the potency of the active component. The composition can, if desired, also contain other compatible therapeutic agents.

In therapeutic use as agents for the treatments as described above, the compounds utilized in the pharmaceutical methods of this invention can be administered at an initial dosage of about 0.01 mg to about 200 mg/kg (amount of agent/kilogram of mammal to be treated) daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Having described the invention herein, listed below are preferred embodiment or working examples wherein all temperatures are degrees Centigrade and all parts are parts by weight unless otherwise indicated.

EXAMPLES

Experimental for Tricyclic quinoxaline 2,3-dione derivatives

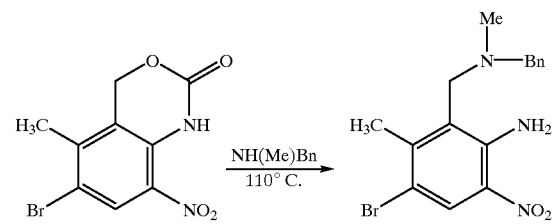

2-[Benzyl-methyl-amino)-methyl]-4-bromo-3-methyl-6-nitro-phenylamine

6-Bromo-5-methyl-8-nitro-1,4-dihydro-benzo[d][1,3] oxazine-2-one (11.48 g, 40 mmol) was heated to 140° C. for 18 hours. TLC (SiO$_2$, pet.ether:EtOAc, 1:1) indicated completion. Volatile material concentrated on rotavap and the dark oil extracted with ethyl acetate (2×250 mL). Solvent evaporated to give viscous oil, which on trituration with ethyl acetate (150 mL) gave yellow crystalline product.

Yield in two crops: 10.17 g=70%. MS (CI): M+1=364. Elemental analysis calculated for: $C_{16}H_{18}BrN_3O_2$: C, 52.76; H, 4.98; N, 11.54. Found: C, 52.22; H, 4.87; N, 11.11.

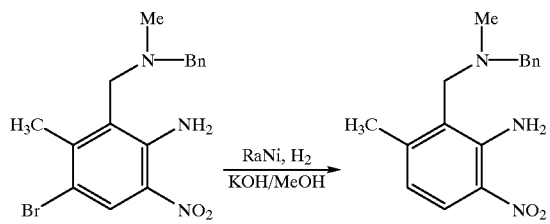

3-[(Benzyl-methyl-amino)-methyl]-4-methyl-benzene-1,2-diamine

2-[(Benzyl-methyl-amino)-methyl]-4-bromo-3-methyl-6-nitro-phenylamine (6 g, 16.5 mmol) was hydrogenated (Ra Ni, 3 g) in the presence of KOH (0.498N). Reaction mixture filtered and extracted in $CHCl_3$ (200 mL) and washed with water and dried ($MgSO_4$). Solvent evaporated to give a dark oil 4.19 g=99%.

H-NMR: 1.96 (s, 3H), 2.08 (s, 3H), 3.36–3.39 (m, 4H), 4.23 (s, 2H), 4.73 (s, 2H), 6.18 (d, 1H, J=7.3 Hz), 6.33 (d, 1H, J=7.3 Hz), 7.21–7.26 (m, 5H).

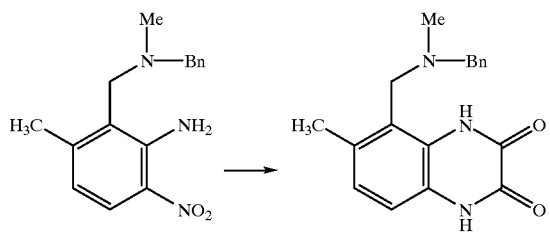

5-[(Benzyl-methyl-amino)-methyl]-6-methyl-1,4-dihydro-quinoxaline-2,3-dione

To a solution of diamine (4.19 g) in THG, dimethyl oxalate (2.36 g, 20 mmol) was added. RM stirred at reflux for 16 hours and cooled. Buff ppt was filtered (2.93 g). Mother liquor gave 2 additional crops. Total yield: 3.94 g=77.4%;

mp 205–206° C. MS (CI): M+1 =310.

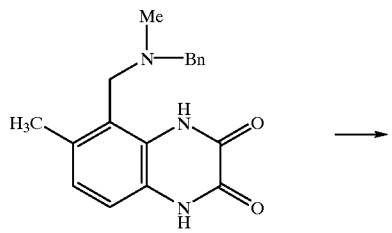

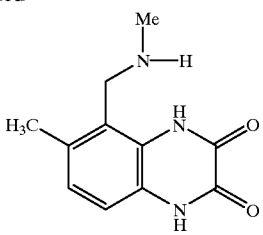

6-Methyl-5-methylaminomethyl-1,4-dihydro-quinoxaline-2,3-dione

A solution of 5-[(benzyl-methyl-amino)-methyl]-6-methyl-1,4-dihydro-quinoxaline-2,3-dione (3.23 g, 10.45 mmol) in DMF (100 mL) was hydrogenated (Pd/C, 20%, 0.5 g) in DMF (100 mL). The suspension was filtered and the filtrate was evaporated to give a solid, which was crystallized from methanol.

Yield: 1.276 g=56%. MS (CI): M+1=220.

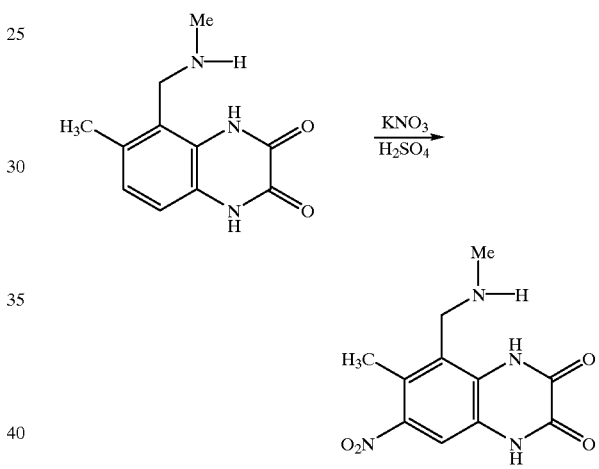

6-Methyl-5-methylaminomethyl-7-nitro-1,4-dihydro-quinoxaline-2,3-dione

To a cooled (10° C.) solution of 6-methyl-5-methalaminomethyl-1,4-dihydro-quinoxaline-2,3-dione (10° C.) of (1.23 g, 5.6 mmol) in conc. $H_2SO_4$ (5 mL), $KNO_3$ (0.60 g, 6 mmol) was added. R<stirred overnight and quenched with ice. Green ppt filtered and washed with ice-cold water and dried (0.77 g, 42%);

mp 260–261° C. MS (CI): M+1=265.

General Method For The Synthesis of Tricyclic Quinoxaline 2,3-Dione Derivatives

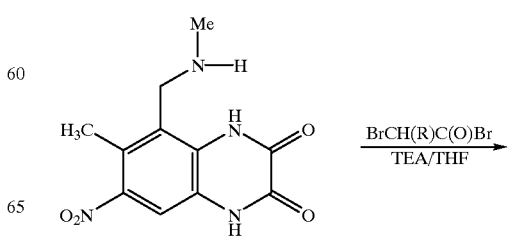

-continued

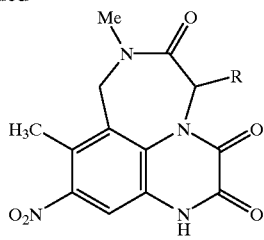

To a solution of 6-methyl-5-methylaminomethyl-7-nitro-1,4-dihydro-quinoxaline2,3-dione (0.1 mmol) and triethylamine (0.3 mmol) in DMF (2 mL), appropriate α-bromoacetyl bromide was added at room temperature under stirring. Reaction was monitored by TLC (SiO$_2$, CHCl$_3$:MeOH, 9:1). On completion, reaction mixture was quenched by water (4 mL) and stirred for about 15 minutes. Precipitate was filtered and air dried and final product was purified by column chromatography (SiO$_2$, CHCl$_3$:MeOH, 100% to 8:2).

Example 1
6-8-Dimethyl-5-nitro-7,8-dihydro-3H-d,8,10a-triaza-cyclohepta[de]naphthalene-1,2,9-trione Following the procedures outlined above the following material was prepared.

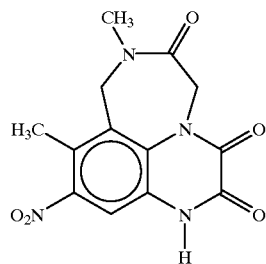

Yield: 51%. MS (CI) (M+1)=305.

Example 2
6,8-Dimethyl-5-nitro-10-phenyl-7,8-dihdro-3H-3,8,10a-triaza-cyclohepta(de)morphthalene-1,2,9-trione Following the procedures outlined above the following material was prepared.

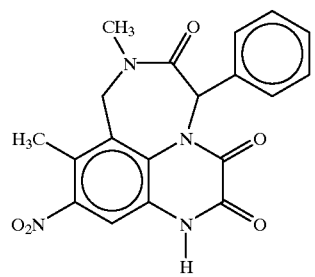

Yield: 52%. MS (CI) (M+1)=381.

BIOLOGICAL ACTIVITY

The compounds of the invention exhibit valuable biological properties because of their strong excitatory amino acid (EAA) antagonizing properties at one of several binding sites on glutamate receptors: the AMPA ((RS)-amino-3-hydroxy-5-methyl-4-isoxazole propionic acid (or kainic acid) binding site on AMPA (non-NMDA) receptors or the glycine site of NMDA receptors.

The compounds of the present invention exhibit binding affinity for the AMPA receptors measured as described in Honore T., et al., *Neuroscience Letters*, 1985;54:27–32. Preferred compounds demonstrate IC$_{50}$ values>100 μM in this assay. The compounds of the present invention exhibit binding affinity for the kainate site (non-NMDA receptor) measured as described in London E. D. and Coyle J., *Mol. Pharmacolo.*, 1979;15:492. The compounds of the present invention exhibit binding affinity for the glycine site of the NMDA receptor measured as described in Jones S. M., et al., *Pharmacol. Methods*, 1989;21:161. To measure functional AMPA antagonist activity, the effects of the agent on AMPA-induced neuronal damage in primary cortical neuronal cultures was examined using techniques similar to those outlined by Koh J. -Y., et al., *J. Neurosci.*, 1990;10:693. In addition, the neuronal damage produced by long-term exposure to 100 μM AMPA may be measured by the release of the cytosolic enzyme lactate dehydrogenase (LDH).

Selected compounds of the present invention were tested by one or more of the above described assays. The data obtained in the assays is set forth in Table 1 below. The IC$_{50}$ values set forth in Table 1 is a measure of the concentration (μM) of the test substance which inhibits 50% of an induced release from the tested receptors.

TABLE 1

|  | Results AMPA | IC$_{50}$ KA | GLY |
|---|---|---|---|
| Compound From Example 1 | 0.85 | 1.55 | 0.2 |
| Compound From Example 2 | 4.5 | 4.9 | 0.6 |

FIG. 1 shows the maximal electroshock time course with the compound from Example 1 in 5 mice given in a dose of 30 mg/kg IV. The graph is the percent of mice protected versus the time in minutes. The solid circle (●) is the compound from Example 1. In a separate experiment the solid square (■) the compound from Example 1 (10 mg/kg, IV) was given to mice (n=5) pretreated with probenecid 30 minutes before the compound. These results are indicative of the in vivo potency of the compound from Example 1 and the effect being positively modulated by ion transporter substrates such as probenecid.

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. A compound of Formula I

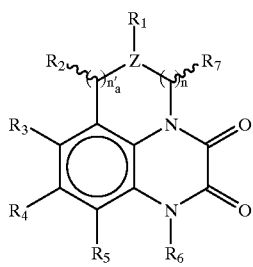

Formula I wherein a is a ring of 6 to 8 members;
n or n' independently is an integer of from 1 to 2;
Z is nitrogen;
$R_1$ is hydrogen,
  alkyl of from 1 to 6 carbon atoms,
  aralkyl of from 7 to 12 carbon atoms,
  carboxyalkyl of from 2 to 8 carbon atoms;
$R_2$ is H or oxygen of carbonyl;
$R_3$ is hydrogen,
  alkyl of from 1 to 6 carbon atoms,
  alkenyl of from 3 to 6 carbon atoms,
  cycloalkyl of from 5 to 7 carbon atoms, or
  halogen,
  haloalkyl of from 1 to 6 carbon atoms,
  aryl of from 6 to 12 carbon atoms,
  aralkyl of from 7 to 12 carbon atoms,
  heteroaromatic ring of from 5 to 8 members which contain nitrogen, oxygen or sulfur,
  heterocyclic ring of from 4 to 7 members which contains nitrogen, oxygen or sulfur,
  nitro,
  cyano,
  $SO_2CF_3$,
  $(CH_2)_m CO_2 R_8$,
  $(CH_2)_m CONR_8 R_9$,
  $SONR_8 R_9$, or
  $NHCOR_8$;
$R_4$ and $R_5$ are each independently
  hydrogen,
  alkyl of from 1 to 6 carbon atoms,
  cycloalkyl of from 5 to 7 carbon atoms,
  alkenyl of from 3 to 6 carbon atoms,
  halogen,
  haloalkyl of from 1 to 6 carbon atoms,
  nitro,
  cyano,
  $SO_2CF_3$,
  $CH_2SO_2R_{10}$,
  $(CH_2)_m CO_2 R_{10}$,
  $(CH_2)_m CONR_{11}R_{12}$,
  $(CH_2)_m SO_2NR_{11}R_{12}$, or
  $NHCOR_6$,
wherein m is an integer of from 0 to 4; and
$R_6$ is hydrogen,
$R_7$ is hydrogen,
  alkyl of from 1 to 6 carbon atoms,
  aralkyl of from 7 to 12 carbon atoms,
  cycloalkyl of from 5 to 7 carbon atoms,
  aryl of from 6 to 12 carbon atoms,
  heteroaromatic ring of from 5 to 8 members containing oxygen, nitrogen or sulfur,
  heterocyclic of from 4 to 7 members containing oxygen, nitrogen or sulfur, or
  oxygen of carbonyl group;
$R_8$ and $R_9$ are each independently hydrogen,
  alkyl of from 1 to 6 carbon atoms,
  cycloalkyl of from 5 to 7 carbon atoms,
  haloalkyl of from 1 to 6 carbon atoms,
  aralkyl of from 7 to 12 carbon atoms; and; either $R_2$ or $R_7$ is an oxygen of carbonyl; and
$R_{10}$, $R_{11}$ and $R_{12}$ are each independently selected from hydrogen,
  alkyl of from 1 to 6 carbon atoms,
  cycloalkyl of from 5 to 7 carbon atoms,
  haloalkyl of from 1 to 6 carbon atoms, or
  aralkyl of from 7 to 12 cabon atoms;
or a pharmaceutical salt thereof.

2. A compound according to claim 1 wherein
a is a ring of 7 members;
n and n' are 1 and 2, respectively;
Z is nitrogen;
$R_7$ is hydrogen,
  alkyl,
  aralkyl,
  cycloalkyl,
  aryl, oxygen of a carbonyl group, or
  heteroaromatic;
$R_1$ is hydrogen or alkyl; and
$R_2$ is hydrogen or the oxygen of a carbonyl group.

3. The compound of claim 1 having the following structure

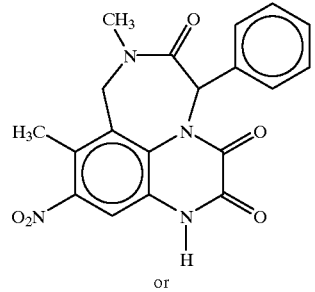

or

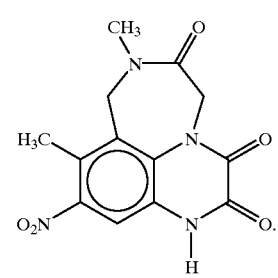

4. The compound of claim 1 wherein $R_3$ is alkyl, and $R_4$ is a nitro group.

5. The compound of claim 1 wherein a is a 7-membered ring.

6. A pharmaceutical composition comprising the compound of claims 1 or 2 and a pharmaceutical carrier.

7. A compound of Formula I

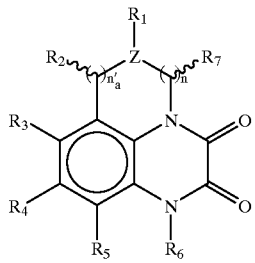

Formula I wherein a is a ring of 7 to 8 members;
n or n' independently is an integer of from 1 to 2;
Z is nitrogen;
$R_1$ is hydrogen,
 alkyl of from 1 to 6 carbon atoms,
 aralkyl of from 7 to 12 carbon atoms, or
 carboxyalkyl of from 2 to 8 carbon atoms;
$R_2$ is H or oxygen of carbonyl;
$R_3$ is hydrogen,
 alkyl of from 1 to 6 carbon atoms,
 alkenyl of from 3 to 6 carbon atoms,
 cycloalkyl of from 5 to 7 carbon atoms,
 halogen,
 haloalkyl of from 1 to 6 carbon atoms,
 aryl of from 6 to 12 carbon atoms,
 aralkyl of from 7 to 12 carbon atoms,
 heteroaromatic ring of from 5 to 8 members which contains nitrogen, oxygen or sulfur;
 heterocyclic ring of from 4 to 7 members which contains nitrogen, oxygen and sulfur,
 nitro,
 cyano,
 $SO_2CF_3$,
 $(CH_2)_m CO_2 R_8$,
 $(CH_2)_m CONR_8 R_9$,
 $SONR_8 R_9$, or
 $NHCOR_8$;
$R_4$ and $R_5$ are each independently
 hydrogen,
 alkyl of from 1 to 6 carbon atoms,
 cycloalkyl of from 5 to 7 carbon atoms,
 alkenyl of from 3 to 6 carbon atoms,
 halogen,
 haloalkyl of from 1 to 6 carbon atoms,
 nitro,
 cyano,
 $SO_2CF_3$,
 $CH_2SO_2R_{10}$,
 $(CH_2)_m CO_2 R_{10}$,
 $(CH_2)_m CONR_{11} R_{12}$,
 $(CH_2)_m SO_2 NR_{11} R_{12}$, or
 $NHCOR_6$,
wherein m is an integer of from 0 to 4; and
$R_6$ is hydrogen, hydroxy, or amino;
$R_7$ is hydrogen,
 alkyl of from 1 to 6 carbon atoms,
 aralkyl of from 7 to 12 carbon atoms,
 cycloalkyl of from 5 to 7 carbon atoms,
 aryl of from 6 to 12 carbon atoms,
 heteroaromatic ring of from 5 to 8, atoms containing oxygen, nitrogen or sulfur,
 heterocyclic ring of from 4 to 7 members containing oxygen, nitrogen or sulfur,
 —$N(R_1)_2$,
 —$SONR_8 R_9$,
 —$NHCOR_8$; or
 a carbonyl group;
$R_8$ and $R_9$ are each independently hydrogen,
 alkyl of from 1 to 6 carbon atoms,
 cycloalkyl of from 5 to 7 carbon atoms,
 haloalkyl of from 1 to 6 carbon atoms,
 aralkyl of from 7 to 12 carbon atoms; and
$R_{10}$, $R_{11}$ and $R_{12}$ are each independently selected from
 hydrogen,
 alkyl of from 1 to 6 carbon atoms,
 cycloalkyl of from 5 to 7 carbon atoms,
 haloalkyl of from 1 to 6 carbon atoms or
 aralkyl of from 7 to 12 carbon atoms; and either $R_2$ or $R_7$ is an oxygen of carbonyl;
or a pharmaceutical salt thereof.

8. A method for the treatment of neurodegenerative disorders selected from the group consisting of ALS, thromboembolic or hemorrhagic stroke, hypoglycemic conditions, cardiac arrest, trauma, ischemia, cerebral infarction, status epileptilus, perinatal asphyxia, anoxia, Lathyrism, Alzheimer's disease, Huntington's Disease, schizophrenia, Parkinsonism, epilepsy, anxiety and pain,
 comprising administering to a mammal in need thereof a therapeutic effective amount of a compound according to claims 1 or 7 and where the compound acts as an antagonist of the AMPA receptor, glycine site of the NMDA receptor and/or the kainate site of the mammal.

* * * * *